(12) United States Patent
Yoder et al.

(10) Patent No.: US 10,820,151 B2
(45) Date of Patent: Oct. 27, 2020

(54) SYSTEM AND METHOD FOR COMPRESSING HIGH FIDELITY MOTION DATA FOR TRANSMISSION OVER A LIMITED BANDWIDTH NETWORK

(71) Applicant: Mars, Incorporated, McLean, VA (US)

(72) Inventors: Nathanael C Yoder, South San Francisco, CA (US); Kevin R Lloyd, San Carlos, CA (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 15/287,544

(22) Filed: Oct. 6, 2016

(65) Prior Publication Data

US 2018/0103349 A1  Apr. 12, 2018

(51) Int. Cl.
| | |
|---|---|
| *H04W 4/02* | (2018.01) |
| *A61B 5/00* | (2006.01) |
| *G16H 40/67* | (2018.01) |
| *H04L 29/06* | (2006.01) |
| *A61B 5/11* | (2006.01) |
| *G01C 22/00* | (2006.01) |
| *H04L 29/08* | (2006.01) |
| *H04W 4/021* | (2018.01) |

(52) U.S. Cl.
CPC .......... *H04W 4/027* (2013.01); *A61B 5/0022* (2013.01); *A61B 5/1118* (2013.01); *A61B 5/7232* (2013.01); *G01C 22/006* (2013.01); *G16H 40/67* (2018.01); *H04L 67/18* (2013.01); *H04L 69/04* (2013.01); *H04W 4/021* (2013.01)

(58) Field of Classification Search
CPC ........ H04W 4/027; H04W 4/021; H04L 67/18
USPC ......................................... 455/456.3; 700/91
See application file for complete search history.

(56) References Cited

U.S. PATENT DOCUMENTS

| | | | |
|---|---|---|---|
| 9,788,232 B2 | 10/2017 | Goldfain et al. | |
| 2003/0065805 A1* | 4/2003 | Barnes, Jr. ............. | G06Q 10/02 709/231 |
| 2008/0240146 A1* | 10/2008 | Singh .................. | H04N 21/4122 370/458 |
| 2012/0296453 A1* | 11/2012 | Prentice ................... | G01S 5/14 700/91 |
| 2013/0174190 A1* | 7/2013 | Ramaswamy .......... | H04L 12/66 725/14 |
| 2014/0156043 A1* | 6/2014 | Blackadar ............ | A61B 5/0024 700/91 |
| 2015/0164377 A1* | 6/2015 | Nathan ................ | A61B 5/1122 600/595 |

(Continued)

*Primary Examiner* — Charles N Appiah
*Assistant Examiner* — Nicole M Louis-Fils
(74) *Attorney, Agent, or Firm* — Mars, Incorporated; Rebecca M. Barnett

(57) ABSTRACT

A system, method, and apparatus for compressing and transmitting motion data. The method comprises receiving high fidelity motion data from a motion sensing device, the high fidelity motion data including a plurality of motion data samples; transmitting the high fidelity motion data to a server; compressing the high fidelity motion data, wherein compressing the high fidelity motion data comprises identifying a subset of the motion data samples and generating a value representing the summary of activity based on the subset of the motion data samples; and transmitting the compressed high fidelity motion data to a server.

17 Claims, 8 Drawing Sheets

(56) References Cited

U.S. PATENT DOCUMENTS

2016/0367202 A1* 12/2016 Carter ..................... A61B 5/02
2017/0251182 A1* 8/2017 Siminoff ................ H04N 7/147
2018/0091630 A1* 3/2018 Yeung .................... H04L 69/04
2018/0103206 A1* 4/2018 Olson .................. H04N 5/2252

* cited by examiner

SYSTEM AND METHOD FOR COMPRESSING HIGH FIDELITY MOTION DATA FOR TRANSMISSION OVER A LIMITED BANDWIDTH NETWORK

COPYRIGHT NOTICE

This application includes material that may be subject to copyright protection. The copyright owner has no objection to the facsimile reproduction by anyone of the patent disclosure, as it appears in the Patent and Trademark Office files or records, but otherwise reserves all copyright rights whatsoever

BACKGROUND

The embodiments described in the disclosure relate to the field of activity or location-based tracking and specifically, to optimizing bandwidth utilization in said field.

With the increase in the use of wearable devices (e.g., smart watches, location trackers, etc.), significant amounts of data are now being collected in real-time by wearable devices. Many of these devices require the transmission of collected data to a server in order to process, analyze, and present visualizations of the raw, collected data.

While the collection and analysis of real-time data (e.g., accelerometer data) provides significant benefits to users of wearable devices (e.g., the ability to monitor movement, track progress, and meet goals), such benefits come at a cost to the user. Specifically, in order provide accurate and comprehensive visualizations, many current systems require the transmission of all, or substantially all, of the captured data from the wearable device to a server-based processing system. For some types of data (e.g., movement data), this can be a significant amount of data. For example, if a wearable device is collecting 1 kilobyte of data every second, a wearable device, in theory, may be transferring approximately 3 megabytes per hour. Further, if the wearable device is transmitting this data over a radio network (e.g., a cellular network), the user may incur substantial expenses to transmit such data.

Such problems are amplified for systems utilized with non-human entities. For example, while humans may be capable of manually controlling the transmission of data, or may be stationary for long periods, wearable devices on non-human entities (e.g., pets) are not subject to such intervention. For example, a wearable tracking device present on a pet may continuously transmit data at all times, and without interruption, in order to accurately monitor the activity of the pet.

Thus, there currently exists a need in the art to remedy the aforementioned deficiencies in wearable device technology. Specifically, these exists a need in the art to reduce the amount of data transmitted over cost-prohibitive networks (e.g., cellular networks) while maintaining the usefulness of the reduced data.

BRIEF SUMMARY

To remedy the aforementioned deficiencies, the disclosure presents systems, methods, and apparatuses for compressing high fidelity motion data for transmission over a limited bandwidth or high-cost network, such as a cellular network.

In one embodiment, the disclosure describes a method for compressing and transmitting motion data. The method includes receiving high fidelity motion data from a motion sensing device, the high fidelity motion data including a plurality of motion data samples; transmitting the high fidelity motion data to a server if a high fidelity transfer event has occurred; compressing the high fidelity motion data, wherein compressing the high fidelity motion data comprises identifying a subset of the motion data samples and generating a value representing the summary of activity based on the subset of the motion data samples; and transmitting the compressed high fidelity motion data to a server.

In one embodiment, the disclosure describes an apparatus for compressing and transmitting motion data. The apparatus includes a processor and a non-transitory memory storing computer-executable instructions therein that, when executed by the processor. The computer-executable instructions cause the apparatus to receive high fidelity motion data from a motion sensing device, the high fidelity motion data including a plurality of motion data samples; transmit the high fidelity motion data to a server if a high fidelity transfer event has occurred; compress the high fidelity motion data, wherein compressing the high fidelity motion data comprises identifying a subset of the motion data samples and generating a value representing the summary of activity based on the subset of the motion data samples; and transmit the compressed high fidelity motion data to a server.

In one embodiment, the disclosure describes a system for compressing and transmitting motion data. The system includes a tracking device, connected to a network, configured to receive high fidelity motion data from a motion sensing device, the high fidelity motion data including a plurality of motion data samples; determine if a high fidelity transfer event has occurred; transmit the high fidelity motion data to a server if a high fidelity transfer event has occurred; compress the high fidelity motion data if a high fidelity transfer event has not occurred, wherein compressing the high fidelity motion data comprises identifying a subset of the motion data samples and generating a value representing the summary of activity based on the subset of the motion data samples; and transmit the compressed high fidelity motion data to a server. The system further includes a server, connected to the network, configured to receive high fidelity and low fidelity motion data from a tracking device; generate one or more visualizations based on the received high fidelity and low fidelity motion data; and transmit the one or more visualizations to a mobile device.

BRIEF DESCRIPTION OF THE DRAWINGS

The foregoing and other objects, features, and advantages of the disclosure will be apparent from the following description of embodiments as illustrated in the accompanying drawings, in which reference characters refer to the same parts throughout the various views. The drawings are not necessarily to scale, emphasis instead being placed upon illustrating principles of the disclosure.

DETAILED DESCRIPTION

Figure 1:
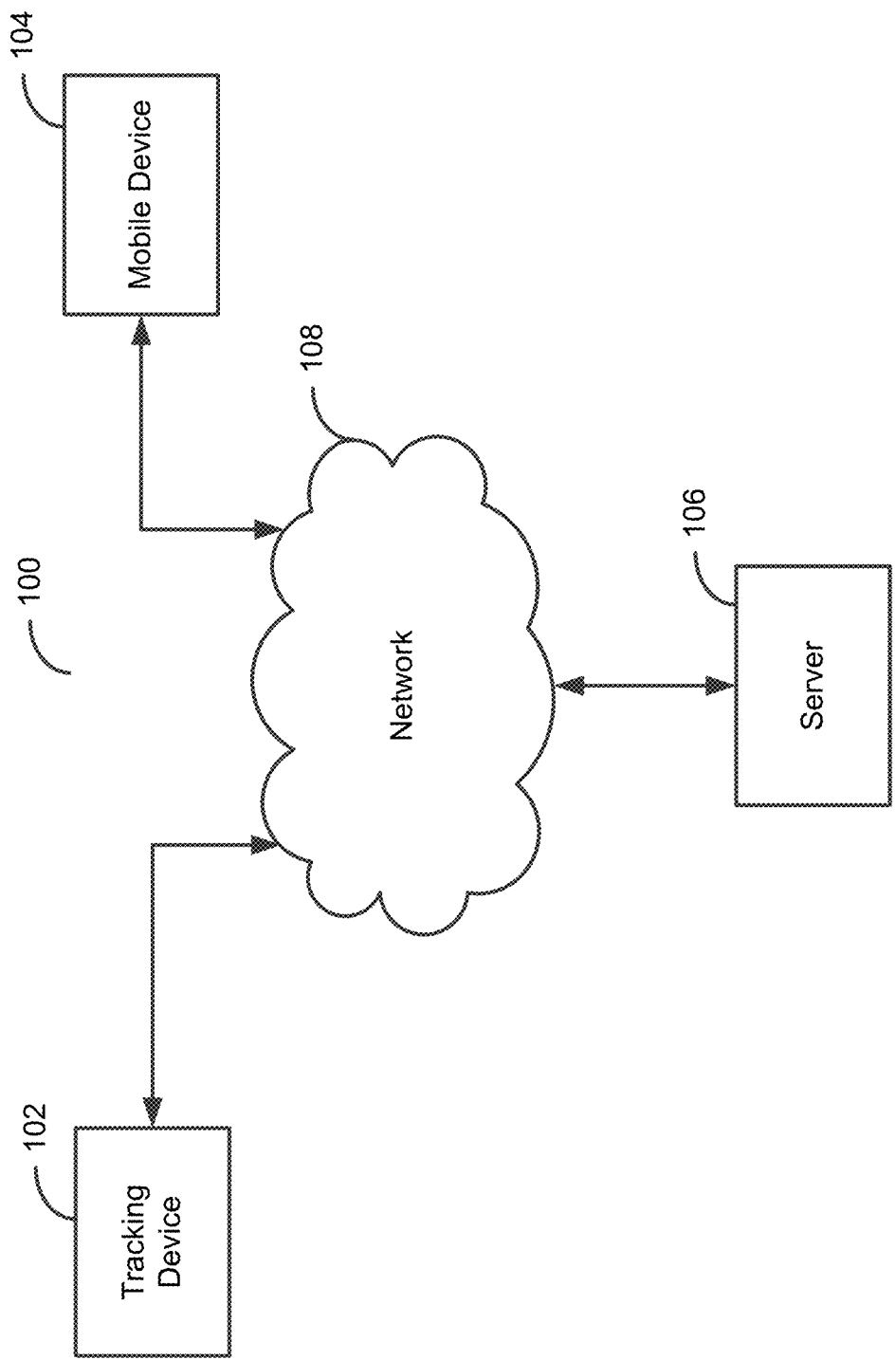
FIG. 1 is a network diagram illustrating a system for transmitting compressed motion data according to some embodiments of the disclosure.

The present disclosure will now be described more fully hereinafter with reference to the accompanying drawings, which form a part hereof, and which show, by way of illustration, certain example embodiments. Subject matter may, however, be embodied in a variety of different forms and, therefore, covered or claimed subject matter is intended to be construed as not being limited to any example embodiments set forth herein; example embodiments are provided merely to be illustrative. Likewise, a reasonably broad scope for claimed or covered subject matter is intended. Among other things, for example, subject matter may be embodied as methods, devices, components, or systems. Accordingly, embodiments may, for example, take the form of hardware, software, firmware or any combination thereof (other than software per se). The following detailed description is, therefore, not intended to be taken in a limiting sense.

Throughout the specification and claims, terms may have nuanced meanings suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

The present disclosure is described below with reference to block diagrams and operational illustrations of methods and devices. It is understood that each block of the block diagrams or operational illustrations, and combinations of blocks in the block diagrams or operational illustrations, can be implemented by means of analog or digital hardware and computer program instructions. These computer program instructions can be provided to a processor of a general purpose computer to alter its function as detailed herein, a special purpose computer, ASIC, or other programmable data processing apparatus, such that the instructions, which execute via the processor of the computer or other programmable data processing apparatus, implement the functions/acts specified in the block diagrams or operational block or blocks. In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

These computer program instructions can be provided to a processor of: a general purpose computer to alter its function to a special purpose; a special purpose computer; ASIC; or other programmable digital data processing apparatus, such that the instructions, which execute via the processor of the computer or other programmable data processing apparatus, implement the functions/acts specified in the block diagrams or operational block or blocks, thereby transforming their functionality in accordance with embodiments herein.

For the purposes of this disclosure a computer readable medium (or computer-readable storage medium/media) stores computer data, which data can include computer program code (or computer-executable instructions) that is executable by a computer, in machine readable form. By way of example, and not limitation, a computer readable medium may comprise computer readable storage media, for tangible or fixed storage of data, or communication media for transient interpretation of code-containing signals. Computer readable storage media, as used herein, refers to physical or tangible storage (as opposed to signals) and includes without limitation volatile and non-volatile, removable and non-removable media implemented in any method or technology for the tangible storage of information such as computer-readable instructions, data structures, program modules or other data. Computer readable storage media includes, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other physical or material medium which can be used to tangibly store the desired information or data or instructions and which can be accessed by a computer or processor.

For the purposes of this disclosure the term "server" should be understood to refer to a service point which provides processing, database, and communication facilities. By way of example, and not limitation, the term "server" can refer to a single, physical processor with associated communications and data storage and database facilities, or it can refer to a networked or clustered complex of processors and associated network and storage devices, as well as operating software and one or more database systems and application software that support the services provided by the server. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

For the purposes of this disclosure a "network" should be understood to refer to a network that may couple devices so that communications may be exchanged, such as between a server and a client device or other types of devices, including between wireless devices coupled via a wireless network, for example. A network may also include mass storage, such as network attached storage (NAS), a storage area network (SAN), or other forms of computer or machine readable media, for example. A network may include the Internet, one or more local area networks (LANs), one or more wide area networks (WANs), wire-line type connections, wireless type connections, cellular or any combination thereof. Likewise, sub-networks, which may employ differing architectures or may be compliant or compatible with differing protocols, may interoperate within a larger network. Various types of devices may, for example, be made available to provide an interoperable capability for differing architectures or protocols. As one illustrative example, a router may provide a link between otherwise separate and independent LANs.

A communication link or channel may include, for example, analog telephone lines, such as a twisted wire pair, a coaxial cable, full or fractional digital lines including T1, T2, T3, or T4 type lines, Integrated Services Digital Networks (ISDNs), Digital Subscriber Lines (DSLs), wireless links including satellite links, or other communication links or channels, such as may be known to those skilled in the art. Furthermore, a computing device or other related electronic devices may be remotely coupled to a network, such as via a wired or wireless line or link, for example.

For purposes of this disclosure, a "wireless network" should be understood to couple client devices with a network. A wireless network may employ stand-alone ad-hoc networks, mesh networks, Wireless LAN (WLAN) networks, cellular networks, or the like. A wireless network may further include a system of terminals, gateways, routers, or the like coupled by wireless radio links, or the like, which may move freely, randomly or organize themselves arbitrarily, such that network topology may change, at times even rapidly.

A wireless network may further employ a plurality of network access technologies, including Wi-Fi, Long Term Evolution (LTE), WLAN, Wireless Router (WR) mesh, or 2nd, 3rd, or 4th generation (2G, 3G, or 4G) cellular technology, or the like. Network access technologies may enable wide area coverage for devices, such as client devices with varying degrees of mobility, for example.

For example, a network may enable RF or wireless type communication via one or more network access technologies, such as Global System for Mobile communication (GSM), Universal Mobile Telecommunications System (UMTS), General Packet Radio Services (GPRS), Enhanced Data GSM Environment (EDGE), 3GPP Long Term Evolution (LTE), LTE Advanced, Wideband Code Division Multiple Access (WCDMA), Bluetooth, 802.11b/g/n, or the like. A wireless network may include virtually any type of wireless communication mechanism by which signals may be communicated between devices, such as a client device or a computing device, between or within a network, or the like.

A computing device may be capable of sending or receiving signals, such as via a wired or wireless network, or may be capable of processing or storing signals, such as in memory as physical memory states, and may, therefore, operate as a server. Thus, devices capable of operating as a server may include, as examples, dedicated rack-mounted servers, desktop computers, laptop computers, set top boxes, integrated devices combining various features, such as two or more features of the foregoing devices, or the like. Servers may vary widely in configuration or capabilities, but generally a server may include one or more central processing units and memory. A server may also include one or more mass storage devices, one or more power supplies, one or more wired or wireless network interfaces, one or more input/output interfaces, or one or more operating systems, such as Windows Server, Mac OS X, Unix, Linux, FreeBSD, or the like.

FIG. 1 is a network diagram illustrating a system for transmitting compressed motion data according to some embodiments of the disclosure. As illustrated in FIG. 1, the system 100 includes a tracking device 102, mobile device 104, server 106, and network 108.

As illustrated in FIG. 1, a tracking device 102 may comprise a computing device designed to be worn, or otherwise carried, by a user or other entity, such as an animal. In one embodiment, the tracking device 102 may include the hardware illustrated in FIG. 2. The tracking device 102 may be configured to collect data generated by various hardware components present within the tracking device 102, such as accelerometers, gyroscopes, or other devices capable of recording motion data regarding the movement or activity of the tracking device 102.

As discussed in more detail herein, tracking device 102 may further include processing logic (e.g., a CPU) capable of receiving and processing the motion data. In some embodiments, the tracking device 102 may specifically be configured to receive motion data and pre-process the motion data prior to transmittal. In addition to recording and processing motion data, tracking device 102 may further be configured to transmit data, including motion data, to other devices via network 108. Specific embodiments of processing and transmitting motion data are described more fully with respect to FIGS. 4 through 6.

Although illustrated as a single network, network 108 may comprise multiple networks facilitating communication between devices. In one embodiment, the network 108 may include a wireless fidelity ("Wi-Fi") network as defined by the IEEE 802.11 standards or equivalent standards. In this embodiment, the network 108 may enable the transfer of motion data from tracking device 102 to server 106. Additionally, the network 108 may facilitate the transfer of data between tracking device 102 and mobile device 104. In an alternative embodiment, the network 108 may comprise a mobile network such as a cellular network. In this embodiment, data may be transferred between the illustrated devices in a manner similar to the embodiment wherein the network 108 is a Wi-Fi network. Notably, however, if network 108 comprises a mobile network, data transfers may be throttled or subject to interference which reduces the bandwidth of the network. Finally, in one embodiment, network 108 may comprise a Bluetooth network. In this embodiment, tracking device 102 and mobile device 104 may be capable of transferring data between themselves. However, server 106 may not be able to communicate with tracking device 102 and mobile device 104. While described in isolation, network 108 may include multiple networks. For example, network 108 may include a Bluetooth network facilitating transfers of data between tracking device 102 and mobile device 104, a Wi-Fi network, and a mobile network.

The system 100 may further include a mobile device 104. In one embodiment, a mobile device 104 may include a mobile phone or tablet device. In alternative embodiments, the system 100 may additionally include laptop computers, desktop computers, or other personal computing devices to perform some of the functions described with respect to mobile device 104. As discussed previously, mobile device 104 may communicate with a tracking device 102 via a Wi-Fi network or Bluetooth network. In these embodiments, mobile device 104 may receive motion data from a tracking device 102 as described in more detail herein. Additionally, tracking device 102 may receive data from mobile device 104. In one embodiment, tracking device 102 may receive data regarding the proximity of mobile device 104 to tracking device 102 or an identification of a user associated with mobile device 104.

Figure 7:
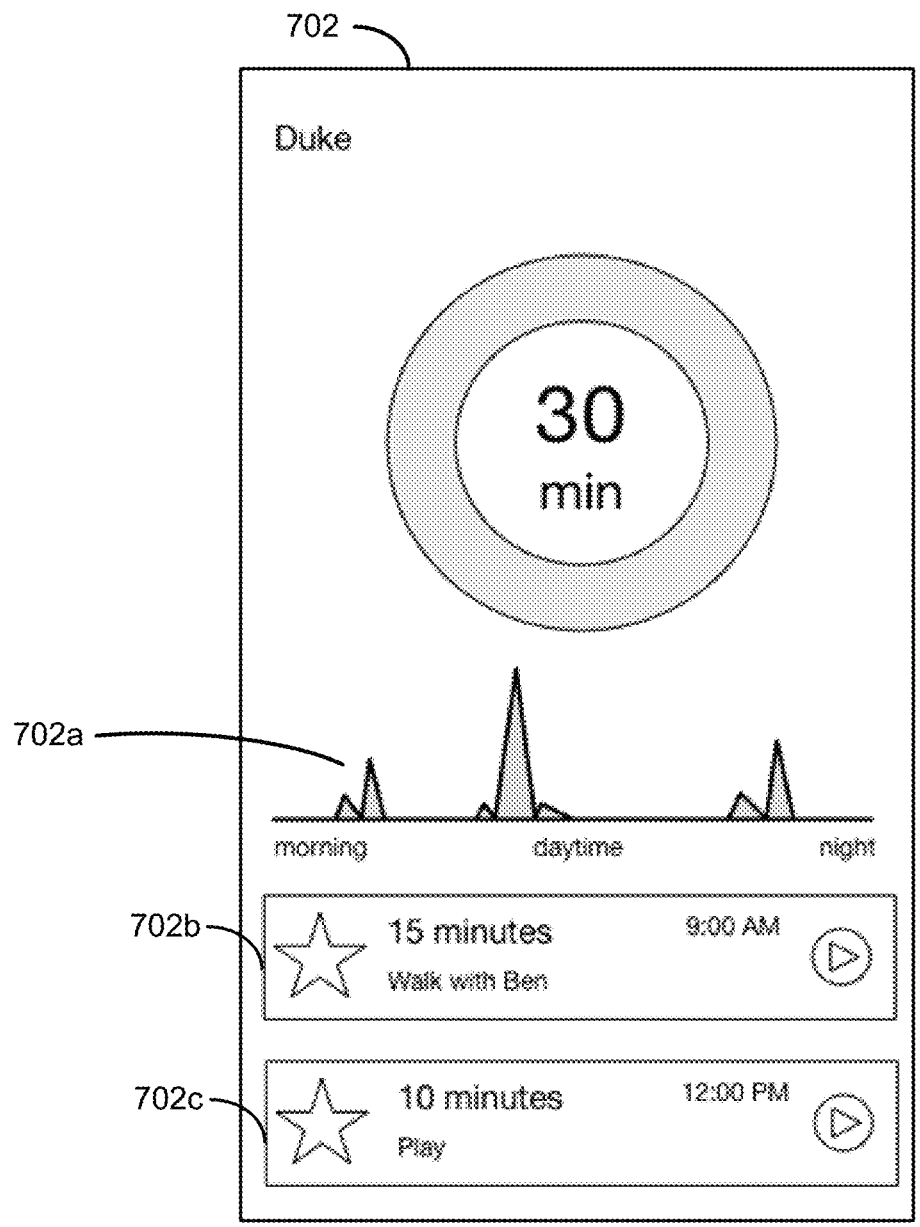
FIG. 7 is illustration of a user interface for displaying activity data according to some embodiments of the disclosure.

Mobile device 104 (or non-mobile device) may additionally communicate with server 106 to receive data from server 106. For example, server 106 may include one or more application servers providing a networked application or application programming interface (API). In one embodiment, mobile device 104 may be equipped with an application that communicates with server 106 via an API to retrieve and present data within the application. In one embodiment, server 106 may provide visualizations of motion data received from tracking device 102. For example, visualization data may include graphs, charts, or other representations of data received from tracking device 102. An example of a mobile application that receives data from server 106 is depicted in FIG. 7.

Figure 2:
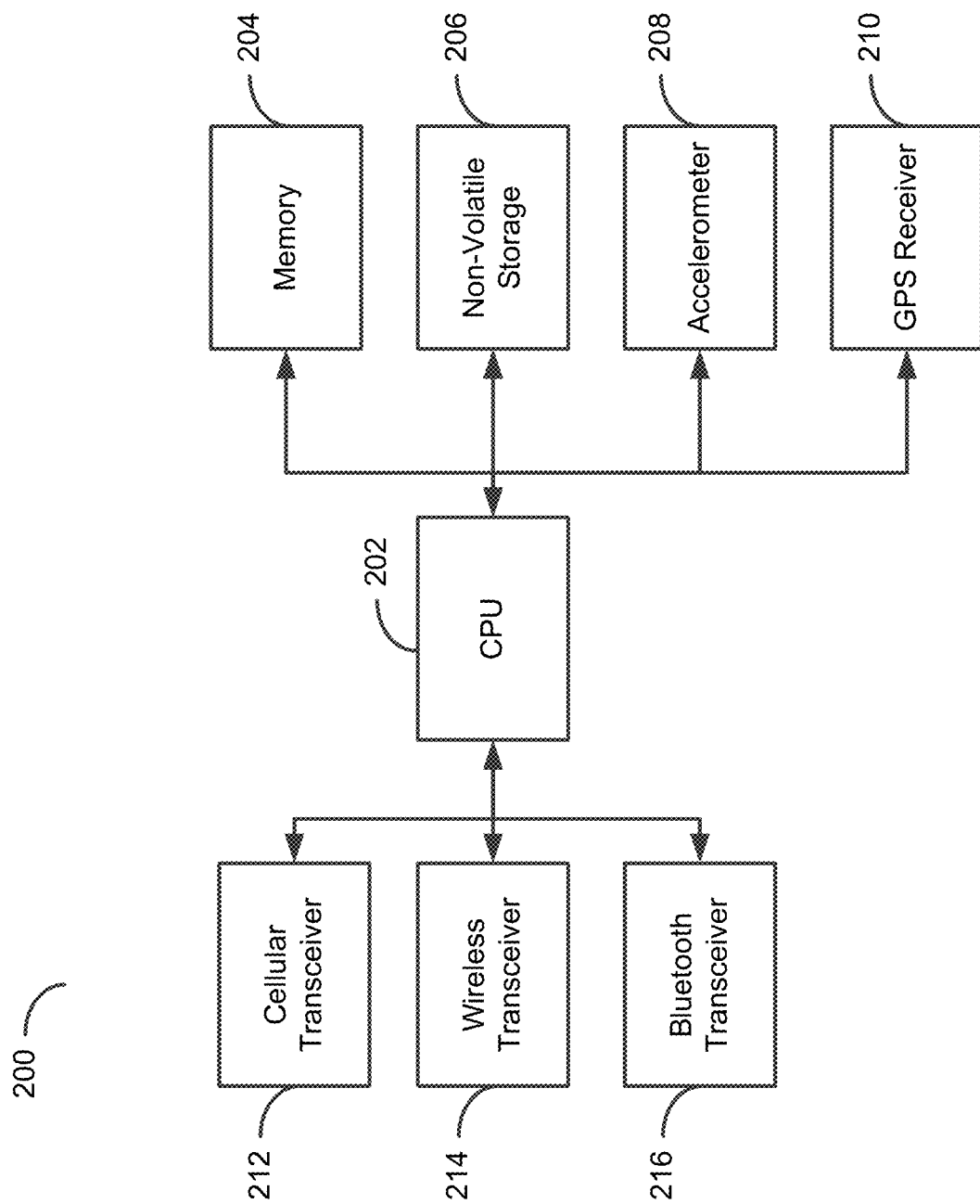
FIG. 2 is a physical diagram illustrating a tracking device for transmitting compressed motion data according to some embodiments of the disclosure.

FIG. 2 is a physical diagram illustrating a tracking device for transmitting compressed motion data according to some embodiments of the disclosure. The device 200 includes CPU 202, memory 204, non-volatile storage 206, accelerometer 208, GPS receiver 210, cellular transceiver 212, Bluetooth transceiver 216, and wireless transceiver 214.

As discussed with respect to FIG. 1, the device 200 may comprise a computing device designed to be worn, or otherwise carried, by a user or entity such as an animal. The device 200 includes an accelerometer 208 and GPS receiver 210 which monitor the device 200 to identify its position (via GPS transceiver 210) and its acceleration (via accelerometer 208). Although illustrated as a single component, accelerometer 208 and GPS transceiver 210 may alternatively each include multiple components providing similar functionality.

Accelerometer 208 generates motion data as described in more detail herein and transmits the motion data to other components via CPU 202. In one embodiment, accelerometer 208 may transmit motion data to CPU 202 for processing as described in more detail with respect to FIGS. 4 through 6. Alternatively, or in conjunction with the foregoing, accelerometer 208 may transmit motion data to memory 204 via CPU 202 for short-term storage. In one embodiment, memory 204 may comprise a random access memory device or similar volatile storage device. Alternatively, or in conjunction with the foregoing, accelerometer 208 may transmit motion data directly to non-volatile storage 206. In this embodiment, CPU 202 may access the motion data directly from memory 204. In some embodiments, non-volatile storage 206 may comprise a solid-state storage device (e.g., a "flash" storage device) or a traditional storage device (e.g., a hard disk). Likewise, GPS receiver 210 may transmit location data (e.g., latitude, longitude, etc.) to CPU 202, memory 204 (via CPU 202), or non-volatile storage 206 (via CPU 202) in similar manners. In some embodiments, CPU 202 may comprise a field programmable gate array or customized application-specific integrated circuit.

As illustrated in FIG. 2, the device 200 includes multiple network interfaces including cellular transceiver 212, wireless transceiver 214, and Bluetooth transceiver 216. As discussed in connection with FIG. 1, cellular transceiver 212 enables the device 200 to transmit motion data, generated by accelerometer 208 and processed by CPU 202, to a server via a mobile or radio network. As discussed more fully with respect to FIG. 6, transmission of data using cellular transceiver 212, wireless transceiver 214, and Bluetooth transceiver 216 may be controlled by the CPU 202 based upon detected network conditions. Additionally, CPU 202 may determine the format and contents of data transferred using cellular transceiver 212, wireless transceiver 214, and Bluetooth transceiver 216 based upon detected network conditions.

Figure 3:
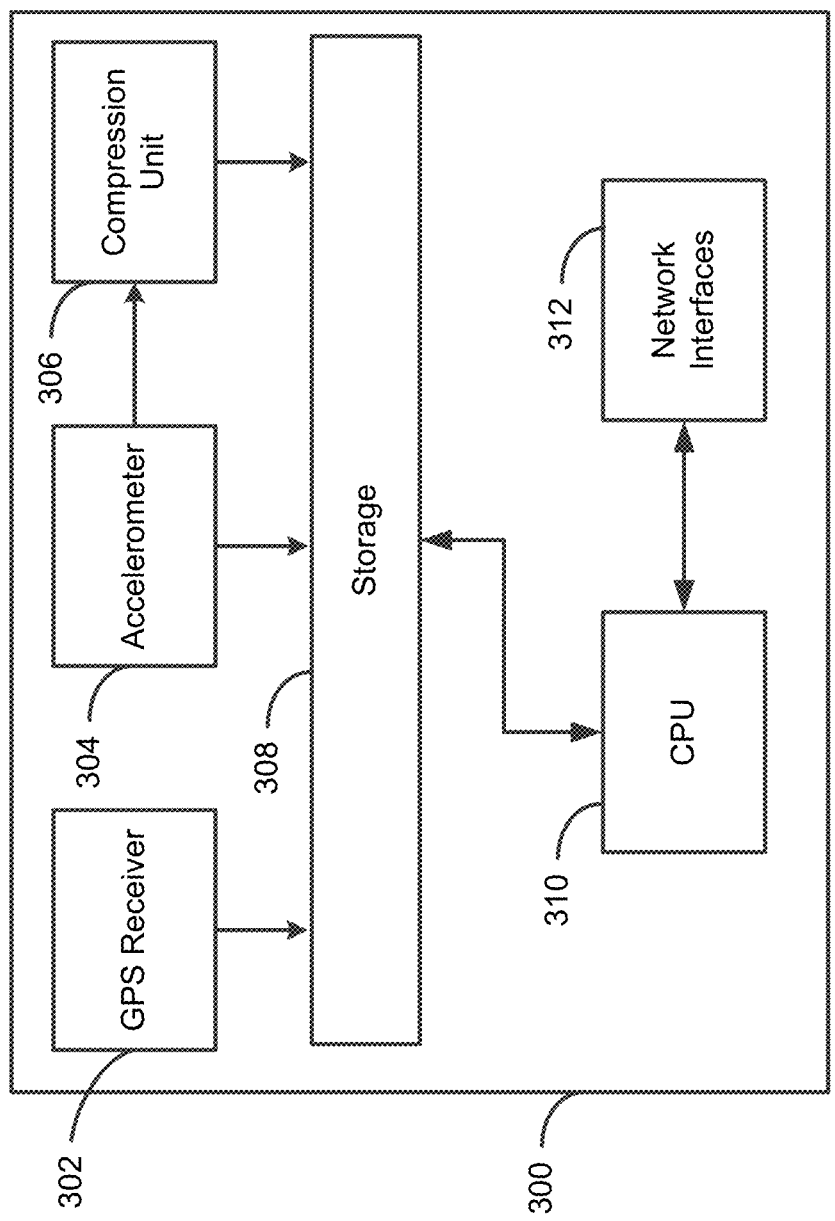
FIG. 3 is a logical block diagram illustrating a tracking device for transmitting compressed motion data according to some embodiments of the disclosure.

FIG. 3 is a logical block diagram illustrating a tracking device for transmitting compressed motion data according to some embodiments of the disclosure. As illustrated in FIG. 3, a device 300 includes a GPS receiver 302, an accelerometer 304, a compression unit 306, storage 308, CPU 310, and network interfaces 312.

In the illustrated embodiment, accelerometer 304 records motion data associated with the device 300 at a predetermined frequency (e.g., 50 Hz). Motion data may include numerous data point representing the movement of the device 300 along a variety of axes (e.g., x-, y-, and z-axes) and may further represent the acceleration of the device with respect to the axes.

Accelerometer 304 may transmit motion data to compression unit 306 and storage 308. In some embodiments, accelerometer 304 may actively transmit, or push, data to compression unit 306 and storage 308. Alternatively, accelerometer 304 may only transmit data to compression unit 306 and storage 308 in response to a request for accelerometer data (e.g., from CPU 310).

Data transmitted between accelerometer 304 and storage 308 may comprise unaltered (e.g., "raw" or "high fidelity") motion data. For example, device 300 may be configured such that all motion data generated by accelerometer 304 is automatically stored in storage 308. Storage 308 may comprise a combination of volatile and non-volatile storage devices as described in more detail in connection with FIG. 2. Alternatively, or in conjunction with the foregoing, CPU 310 may monitor the storage capacity of storage 308 and only permit the transfer of motion data from accelerometer 304 to storage 308 if storage 308 contains excess capacity. Alternatively, CPU 310 may actively manage the excess capacity of storage 308 to ensure the availability of excess capacity. For example, CPU 310 may proactively "flush" data stored in storage 308 upon the detection of a high bandwidth network connection. In this manner, CPU 310 may operate storage 308 as a cache in between periods wherein a high bandwidth connection is available. In alternative embodiments, accelerometer 304 and GPS receiver 302 may communicate directly with CPU 310, rather than communicating through storage 308. In this embodiment, data from accelerometer 304 and GPS receiver 302 may be transmitted directly to CPU 310, processed by CPU 310, and stored within storage 308 (e.g., within a Flash memory storage area).

In addition to the foregoing, accelerometer 304 may be configured to transmit motion data to compression unit 306. Compression unit 306 may, in turn, compress the received motion data to generate compressed (or "low fidelity") motion data. Compression unit 306 then stores the low fidelity motion data in storage 308. Compression of motion data is described more fully in connection with FIGS. 4 and 5, the discussion of which is incorporated fully herein in its entirety. In one embodiment, compression unit 306 may be implemented within CPU 310. For example, compression unit 306 may comprise a software module executed by CPU 310. In this embodiment, accelerometer data generated by accelerometer 304 may be transmitted directly to CPU 310 wherein compression unit 306, executing on CPU 310, may compress the accelerometer data as discussed herein.

In alternative embodiments, the device 300 may only store one of high fidelity or low fidelity data, rather than storing both. For example, device 300 may be configured to only store high fidelity motion data when connected to a low bandwidth network, in order to save the high fidelity motion data, while "streaming" low fidelity motion data over a network via network interfaces 312. Likewise, if connected to a high bandwidth network, device 300 may simply transmit high fidelity motion data over network via network interfaces 312 without storing the high fidelity motion data.

CPU 310 is capable of controlling access to storage 308, retrieving data from storage 308, and transmitting data to a networked device via network interfaces 312. Additionally CPU 310 is responsible for monitoring the bandwidth conditions of a network and dynamically selecting whether to send high or low fidelity motion data in response to network bandwidth constraints. Additionally, CPU 310 is responsible for identifying trigger conditions or events that enable the transfer of high fidelity motion data over a low bandwidth network. In one embodiment, CPU 310 may monitor data received from GPS receiver 302 to identify that the device 300 has exited a geo-fenced area. In response, CPU 310 may retrieve locally stored high fidelity motion data and begin transmitting the high fidelity motion data over a low bandwidth network (e.g., a cellular network). Identifying trigger conditions or events is described more fully in connection with FIG. 6, the discussion of which is incorporated fully herein in its entirety.

For example, in a scenario where device 300 is implemented as a tracking device on an animal's collar, a user may design a geo-fence corresponding to the property lines of the user's property or a subset thereof. Alternatively, a geo-fence may be generated automatically based on monitoring the strength of a Wi-Fi network at a predefined location (e.g., a user's home). While within the geo-fenced region, the device 300 may transmit high fidelity motion data over a wireless interface, as the wireless network provides high-speed broadband access at no extra service cost (as compared to cellular networks). However, at some point, an animal equipped with the device 300 may exit the geo-fenced region. In one embodiment, the CPU 310 may identify the exit by monitoring the latitude and longitude of the device received from GPS receiver 302 and comparing the coordinates to the geo-fence coordinates. Alternatively, the CPU 310 may identify the exit by detecting a loss of Wi-Fi signal. In response, the CPU 310 may cease transmitting data using a Wi-Fi interface and may begin transmitting data over a cellular interface. In addition, CPU 310 may transmit only low fidelity motion data over the cellular interface and may throttle the frequency in which such transmissions are made. In this manner, the CPU 310 limits the amount of data transmitted and thus limits the costs incurred by the device 300. Finally, the CPU 310 may subsequently detect the device has re-entered the geo-fenced area. As with detecting an exit, the CPU 310 may detect re-entry by detecting the presence of a known Wi-Fi network or by analyzing the GPS coordinates of the device. In response to the re-entry, the CPU 310 may revert to transmission of high fidelity motion data over a wireless or Bluetooth network.

Although illustrated in the alternative, in one embodiment, the device 300 may further be configured to transmit both high fidelity and low fidelity motion data when connected to a high bandwidth network. In this embodiment, the transmission of both high fidelity and low fidelity motion data may allow a server-side processing routine to improve the compression techniques used by compression unit 306.

Figure 4A:
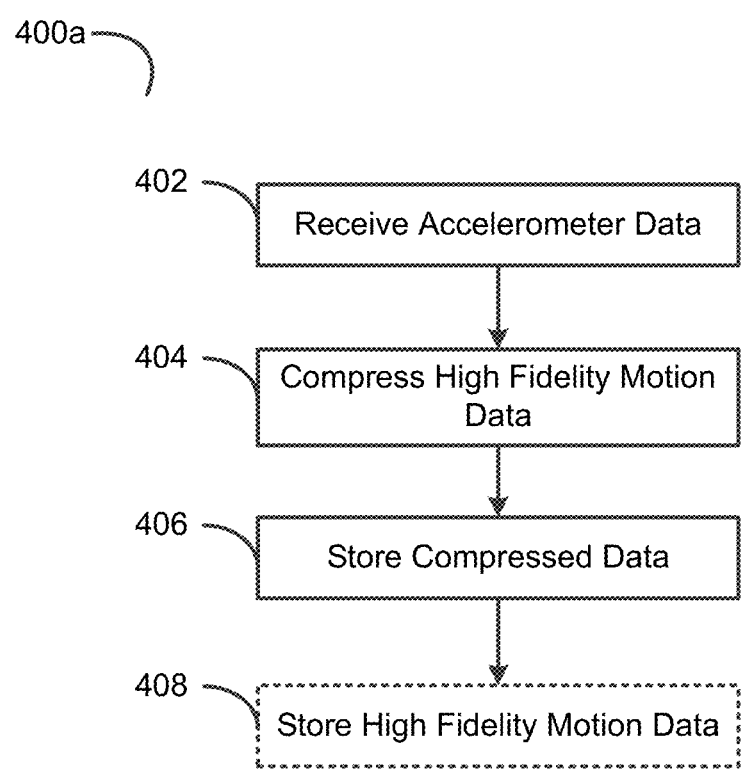
FIG. 4A is a flow diagram illustrating a method for compressing and storing motion data according to some embodiments of the disclosure.

FIG. 4A is a flow diagram illustrating a method for compressing and storing motion data according to some embodiments of the disclosure.

In step 402, the method 400a receives accelerometer data. In one embodiment, accelerometer data comprises a multi-dimensional set of data points generated by an accelerometer device at a predefined frequency. For example, accelerometer data may comprise three-dimensional data corresponding to movement of a device housing the accelerometer device. That is, the accelerometer data may include data point on x-, y-, and z-axes. Specifically, for each axis, accelerometer data may indicate the acceleration of the device along each axis as a floating point value. In some embodiments, accelerometer data may further include gyroscope data measuring rotation around each of said axes. As described previously, accelerometer data may be generated by one or more accelerometers and transmitted over a data bus to a processor or other device. In one embodiment, the method 400a may receive accelerometer data at predefined intervals based on the frequency rate of the accelerometer (e.g., the accelerometer may be polled by a CPU or other device). Alternatively, the method 400a may receive accelerometer data as a stream (or "fire hose") of data points.

In step 404, the method 400a compresses high fidelity motion data. In one embodiment, compressing high fidelity motion data may comprise analyzing a set of individual motion data points and converting the set of individual points into a single value (or data structure) representing the summary of activity represented by the set of individual points. For example, if the motion data received in step 402 is sampled over a period of one minute and contains three thousand data points (e.g., at 50 Hz) in three directions (e.g., x, y, and z) for a total of 9,000 data points, the method 400a may compress these 9,000 data points into a single value representing the summary of activity during that time period. For example, if all 9,000 data points exhibit little or no change, the method 400a may compress the data points by indicating an activity level of zero (0) which may include a number (e.g., 0) and/or other values (e.g., a textual representation such as, "at rest") that significantly compress the original data. Conversely, if the 9,000 data points indicate an acceleration along the x- or y-axes, the method 400a may compress the data points into an integral representation of the velocity. For example, changes in velocity may be ranked on a scale of 1 to 10 indicating the level of activity and/or may include a short description (e.g., "running," "walking," or, for z-axis changes, "jumping"). The compression performed in step 404 is described more fully with respect to FIG. 5 and is not repeated herein for the sake of clarity.

After compressing the high fidelity motion data in step 406, the method 400a stores the compressed data. As discussed previously, storing compressed data may comprise storing the compressed data in volatile memory and/or non-volatile storage. In one embodiment, the method 400a may store compressed data in non-volatile storage upon detecting a lack of network access. Alternatively, the method 400a may forego storing low fidelity data upon detecting network access.

In step 408, the method 400a optionally stores high fidelity data. High fidelity motion data may comprise raw accelerometer data along multiple axes. In alternative embodiments, high fidelity motion may comprise compressed accelerometer data, wherein the raw accelerometer data is compressed using a lossless or substantially lossless compression algorithm. In one embodiment, the method 400a stores all data received in step 402 in memory or in non-volatile storage. In alternative embodiments, the method 400a may only store high fidelity motion data in memory and may forego longer-term storage. For example, the method 400a may bypass the storing of high fidelity motion data if it is detected that a high bandwidth network connection is available (e.g., a Wi-Fi). Alternatively, the method 400a may additionally only store high fidelity motion data upon determining that enough capacity exists for each high fidelity motion data point. In alternative embodiments, the method 400a may clean the received data prior to storing. For example, the method 400a may filter anomalous data points or perform other cleaning operations on the received data.

Figure 4B:
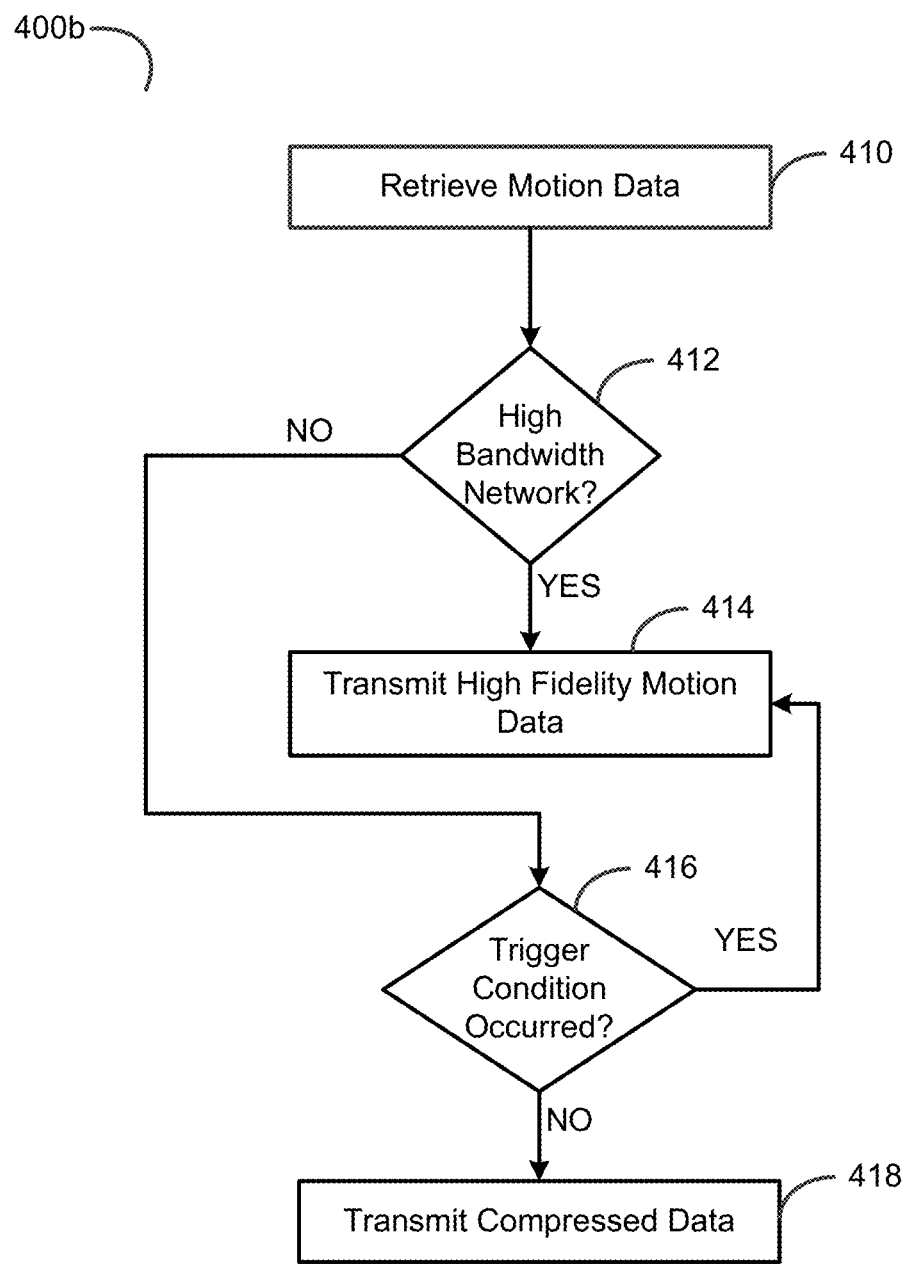
FIG. 4B is a flow diagram illustrating a method for transmitting stored motion data according to some embodiments of the disclosure.

FIG. 4B is a flow diagram illustrating a method for transmitting stored motion data according to some embodiments of the disclosure.

In step 410, the method 400b retrieves motion data. In one embodiment, the method 400b may retrieve motion data generated according to the process depicted in FIG. 4A. In one embodiment, the retrieval of high fidelity motion data may be done on a streaming or batch basis. For example, the method 400b may spool high fidelity motion data until a predetermined amount of data has been spooled prior to transmitting. In one embodiment, the method 400b may be executed concurrently with the method 400a. Alternatively, the method 400b may be executed serially with method 400a.

In step 412, the method 400b detects if a high bandwidth network is available. In one embodiment, step 412 may comprise receiving an indication that a device implementing the method 400b illustrated in FIG. 4B is connected to a high-bandwidth network (e.g., Wi-Fi). That is, step 412 may comprise querying the status of a wireless network adapter to determine if the adapter is connected to a wireless or Bluetooth network.

In step 414, if the method 400b determines that a high-bandwidth network is available, the method 400b may then transmit the high fidelity motion data to, for example, a server device.

As illustrated above, step 412 prevents the transmission of high fidelity (and thus, large volume) motion data if the method 400b determines that the current network is a constrained network (i.e., a network that provides limited bandwidth and/or high costs per unit transferred). However, the method 400b may continue to transfer high fidelity motion data under certain circumstances despite being connected to a low bandwidth network. Specifically, in step 416, the method 400b determines whether a trigger condition occurs. In the illustrated embodiment, a trigger condition is an event or interrupt that forces the method 400b to transmit high fidelity motion data over a low bandwidth network. For example, a user may explicitly request that the method 400b transfer high fidelity motion data over a low bandwidth network. Alternatively, or in conjunction with the foregoing, a preset timer may automatically transmit any stored high fidelity motion data over a low bandwidth network after the timer expires (in order to prevent storage overflow). Additional trigger conditions are discussed more fully with respect to FIG. 6 and are not repeated herein for the sake of clarity.

If the trigger condition occurs, the method 400b transmits high fidelity motion data, as discussed previously with respect to step 414. Alternatively, if the method 400b fails to detect the occurrence of a trigger condition in step 416, the method 400b transmits compressed data, step 418.

In step 418, the method 400b transmits the compressed data. In one embodiment, transmitting the compressed data may comprise transmitting the compressed data (e.g., a numerical value) according to a predefined interval (e.g., once every minute). As discussed previously, the method 400b may transmit compressed data only when connected to a low bandwidth network. In alternative embodiments, the method 400b may additionally transmit data when connected to a high bandwidth network in order to improve step 404 of FIG. 4A as discussed previously.

Figure 5:
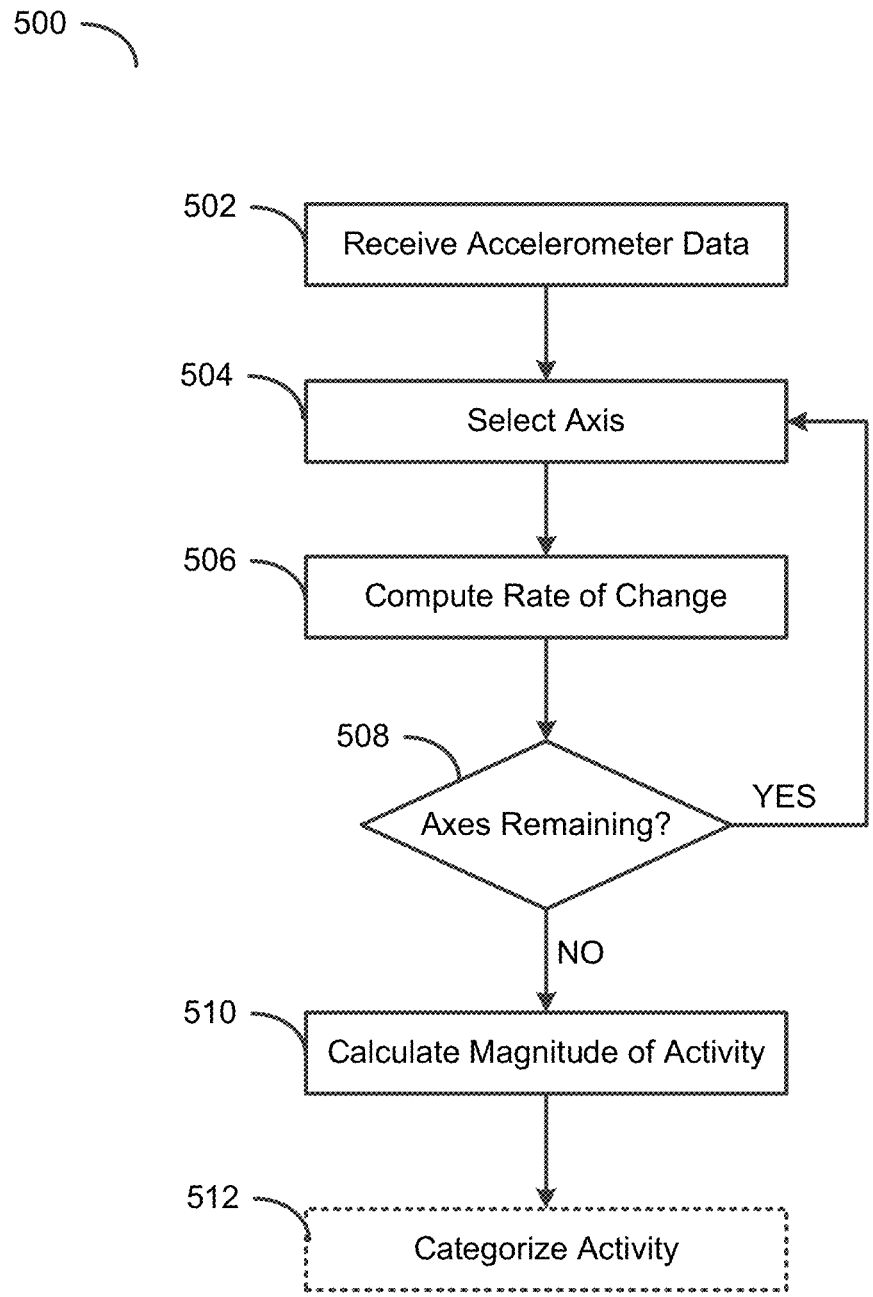
FIG. 5 is a flow diagram illustrating a method for compressing motion data according to some embodiments of the disclosure.

FIG. 5 is a flow diagram illustrating a method for compressing motion data according to some embodiments of the disclosure.

In step 502, the method 500 receives accelerometer data. In the illustrated embodiment, the method 500 may receive a set of data points corresponding to a predefined interval. For example, the method 500 may be invoked once per minute. In one embodiment, the method 500 receives accelerometer data from a storage device such as memory or non-volatile storage device as discussed previously.

In step 504, the method 500 selects an axis identified in the accelerometer data. As discussed previously, accelerometer data may include acceleration data for a plurality of axes (e.g., x-, y-, and z-axes) over a given time interval (e.g., one minute).

In step 506, the method 500 computes a rate of change for data associated with the selected axis. Since the data for a given axis comprises a time-series of acceleration data points, the method 500 may compute a rate of change by determining the slope and/or magnitude of the data points. As one example, the method 500 may determine that for all data points along a given axis the acceleration is zero and may thus compute a rate of change of zero indicating that velocity was constant. As a second example, the method 500 may determine that for all data points along a given axis the acceleration was a constant value and thus may indicate a rate of change equal to the average acceleration. As third example, the method 500 may integrate the received data point to calculate the velocity and record the velocity as the rate of change. Notably, the preceding examples are not intended to be exhaustive and other techniques may exist to convert a list of acceleration data points to a value representing the movement of a device.

After computing the rate of change in step 506, the method 500, in step 508, determines if any axes remain, step 508, and calculates the rate of change for each remaining axis. In one embodiment, the method 500 may simply ignore remaining axes upon determining movement based on the rate of change of another axes. That is, upon determining movement along the x-axis, the method 500 may ignore the y- and z-axes.

In step 510, the method calculates a summary of activity based on the computed rates of change. For example, the method 500 may combine the rates of change into an aggregate rate of change across all axes. Alternatively, the method 500 may average the rates of change across each axis to determine the average rate of change across all axes. Additionally, the method 500 may normalize the calculated rates of change to obtain a summary of activity bounded within a predefined range. For example, the method 500 may normalize rates of changes and classify the rates of changes according to a 0 to 10 scale (e.g., 0 representing no movement, and 10 representing intense movement).

In step 512, the method 500 may optionally categorize the activity. In one embodiment, the method 500 may determine that movement along one axes represents a type of activity while movement along other axes represents other activities. For example, the method 500 may determine that little movement on the x- and y-axes combined with substantial movement on the z axis may representing a "jumping" activity. Alternatively, or in conjunction with the foregoing, the method 500 may assign a textual label to the activity (e.g., "running," "walking," etc.) and combine the textual label with the calculated summary of activity.

As the above description of FIG. 5 illustrates, the method 500 allows for substantial compression of motion data while retaining actionable information regarding the motion data. As discussed previously, for a given minute, accelerometer data may generate a significant amount of data when collecting data. For example, if data points on a given axis are represented by four-byte floating point values, a single sample comprises at least twelve-bytes of information. Captured at 50 Hz, this would generate 600 bytes of information per second, the equivalent of approximately 36 kilobytes per minute, two megabytes per hour, 52 megabytes per day, and 1.5 gigabytes per month. Even by reducing the sampling period of raw motion data to once per minute results in approximately 1 megabyte of high fidelity motion data per day. In contrast, many cellular data plans provided with wearable devices have significantly lower data limits, often times as low as 500 kilobytes of data transfer per month.

By implementing the compression techniques illustrated in FIG. 5, significant compression can be obtained and data can be transmitted over a cellular network without incurring overage fees. For example, if a compressed data packet includes a single four-byte summary of activity value transmitted every minute, monthly data transfers are reduced by multiple orders of magnitude to approximately 173 kilobytes. Even increasing the compressed data size to ten kilobytes per minute (e.g., to account for additional information) results in a monthly transfer amount of approximately 432 kilobytes.

Notably, however, transmitting only compressed data would necessarily result in a loss of granularity. Thus, the embodiments disclosed herein describe techniques for intelligently toggling between the transfer of low fidelity data and high fidelity data, as described in more detail in connection with FIG. 6.

Figure 6:
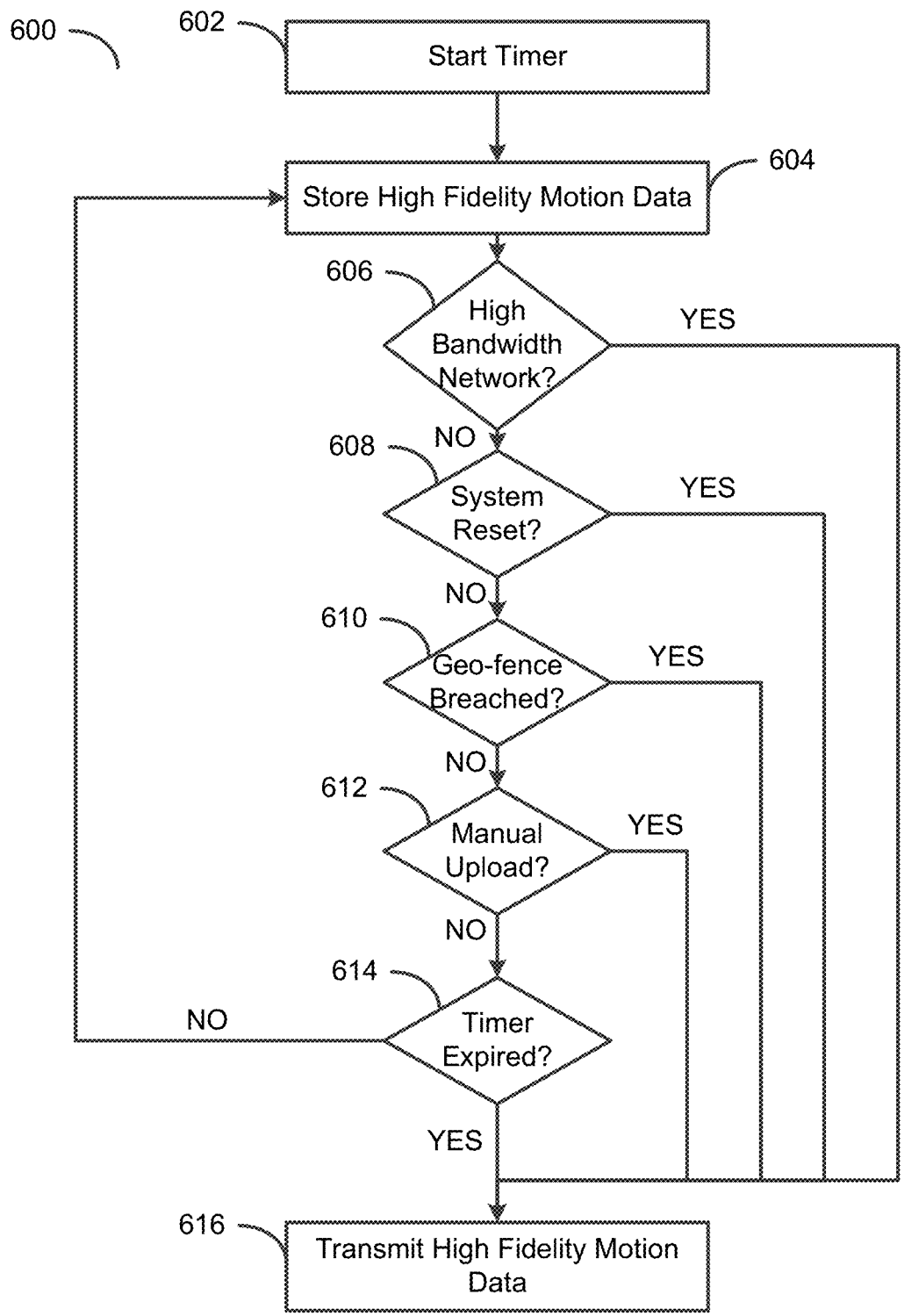
FIG. 6 is a flow diagram illustrating a method for detecting a high fidelity transfer event according to some embodiments of the disclosure.

FIG. 6 is a flow diagram illustrating a method for detecting a high fidelity transfer event according to some embodiments of the disclosure.

In step 602, the method 600 starts a timer and, in step 604, stores high fidelity motion data. In the illustrated embodiment, the stored high fidelity motion data comprises raw data received from an accelerometer, as discussed previously. Although illustrated as sequential steps, steps 602 and 604 may be explicitly executed concurrently in different processes and communication of a timer expiry may be performed in a concurrent fashion In steps 606 through 614, the method 600 determines if any conditions exist that require the transmittal of high fidelity motion data in step 616. As discussed previously, while the method 600 determines that no conditions exist (in step 614), the method 600 may continue to store high fidelity motion data. Concurrently, compressed data corresponding to the stored motion data may be transferred as described in more detail in connection with FIGS. 4 and 5. As will be discussed, each of the triggers or conditions in steps 606 through 614 may cause the method 600 to transmit high fidelity data. Additionally, the occurrence of a trigger or satisfaction of a condition may additionally trigger additional actions not illustrated in FIG. 6 but discussed previously. For example, in addition to transmitting data in step 616, the method 600 may further flush the storage of high fidelity motion data in order to manage storage capacity. Alternatively, or in conjunction with the foregoing, the method 600 may additionally transmit compressed data along with high fidelity motion data in step 616.

In step 606, the method 600 determines if a high bandwidth network is available. If so, the method 600 transmits the stored high fidelity motion data in step 616, and if not the method 600 continues to step 608. In one embodiment, determining if a high bandwidth network is available may comprise monitoring the status of a wireless transceiver to determine if the transceiver is connected to a known (or public) wireless network. In alternative embodiments, determining if a high bandwidth network is available may comprise determining if a Bluetooth connection is available between a tracking device and a mobile device.

In step 608, the method 600 determines if a system reset event has been triggered. If so, the method 600 transmits the stored high fidelity motion data in step 616, and if not the method 600 continues to step 610. In one embodiment, a system reset may comprise the restarting of the device implementing the method 600. For example, the method 600 may detect that an operating system of a device implementing the method 600 was uncleanly restarted and may automatically attempt to transmit high fidelity motion data. In this example, the method 600 may transmit high fidelity motion data in anticipation of possible device corruption or loss of data. In some embodiments, the system reset event may comprise an event indicating that a device may subsequently restart (e.g., due to updates or unexpectedly). In these embodiments, the method 600 may transmit high fidelity motion data in order to prevent data loss or corruption, or to increase storage capacity for updates.

In step 610, the method 600 determines if a geo-fence has been breached. If so, the method 600 transmits the stored high fidelity motion data in step 616, and if not the method 600 continues to step 612. As described previously, in some embodiments, the method 600 may determine that the device implementing the method 600 has breached a geo-fence by detecting the loss of a Wi-Fi signal or using a GPS location. In these embodiments, the breaching of a geo-fence may indicate an emergency condition (e.g., the straying of an animal) that requires higher fidelity motion data in order to monitor the position and movement of the device implementing the method 600. Thus, the method 600 may enable high fidelity motion data transmission upon the device breaching a geo-fence and may subsequently disable high fidelity motion data transfer upon re-entry into a geo-fenced region.

In step 612, the method 600 determines if a user has requested a manual upload of high fidelity motion data. If so, the method 600 transmits the stored high fidelity motion data in step 616, and if not the method 600 continues to step 614. As illustrated in step 612, a user may proactively request the transmission of high fidelity motion data. For example, a remote user may wish to view higher fidelity data regarding the movement of a pet and thus may request the transmission of high fidelity motion data despite the increased costs over transferring high fidelity motion data over a radio network.

In step 614, the method 600 determines if the timer has expired. If so, the method 600 transmits the stored high fidelity motion data in step 616, and if not the method 600 continues store high fidelity motion data in step 604. If none of the preceding triggers or conditions are met, the method 600 may automatically transmit high fidelity motion data if a predetermined amount of time has elapsed. In one embodiment, rather than monitoring the storage capacity, the method 600 may assign a known amount of storage space for high fidelity motion data. By assigning a fixed amount of storage space (e.g., in a separate flash storage device), the method 600 may be able to calculate the maximum amount of cellular transmission time and may set a timer accordingly in order to flush local storage.

Notably, the above triggers and conditions 606 through 614 may be used jointly or separately and in varying combinations depending on actual needs. Additionally, further triggers and conditions may be utilized according to environmental, technical, or user needs. The above-described triggers or conditions are thus not meant to serve as limiting the scope of triggers and conditions used by the method 600 but rather as examples of triggers and conditions used by the method 600.

FIG. 7 is an illustration of a user interface for displaying activity data according to some embodiments of the disclosure.

Screen 702 illustrates a user interface displaying a time-series view of activity of a pet equipped with a tracking device disclosed in the various embodiments and implementing the methods described previously. As illustrated in screen 702, a graphical timeline 702a of activity is presented which illustrates the amount of movement throughout a day. As discussed supra, the timeline 702a may be generated based on compressed data received by a server. Specifically, the summary of activity values may represent the y-axis in timeline 702a, while time represents the x-axis. As discussed previously, high fidelity motion data may be utilized to further refine the timeline 702a.

Screen 702 additionally illustrates detailed events 702b and 702c. Specifically, event 702b illustrates a "Walk" event and 702c illustrates a "Play" event. As discussed previously, the compressed data transmitted to a server may indicate an activity classification derived from the high fidelity motion data. For example, walk event 702b may be classified as such due to continuous movement at a moderate rate. In contrast, play event 702c may be classified as such due to high acceleration followed by short periods of inactivity. In contrast, in the embodiment where the tracking device only transmits a summary of activity value, events 702b and 702c may only be determined upon receiving high fidelity motion data. In this embodiments, events 702b and 702c may only include a time stamp and duration and may omit the event type until receiving the high fidelity motion data.

For the purposes of this disclosure a module is a software, hardware, or firmware (or combinations thereof) system, process or functionality, or component thereof, that performs or facilitates the processes, features, and/or functions described herein (with or without human interaction or augmentation). A module can include sub-modules. Software components of a module may be stored on a computer readable medium for execution by a processor. Modules may be integral to one or more servers, or be loaded and executed by one or more servers. One or more modules may be grouped into an engine or an application.

For the purposes of this disclosure the term "user", "subscriber" "consumer" or "customer" should be understood to refer to a user of an application or applications as described herein and/or a consumer of data supplied by a data provider. By way of example, and not limitation, the term "user" or "subscriber" can refer to a person who receives data provided by the data or service provider over the Internet in a browser session, or can refer to an automated software application which receives the data and stores or processes the data.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible.

Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure.

What is claimed is:

1. A method for compressing and transmitting motion data, the method comprising:

receiving high fidelity motion data from a motion sensing device, the high fidelity motion data including a plurality of motion data samples for a plurality of axes;

storing the high fidelity motion data received from the motion sensing device;

determining whether a network adapter is connected to a high bandwidth network;

transmitting the high fidelity motion data to a server if the network adapter is connected to the high bandwidth network;

detecting that the network adapter has disconnected from the high bandwidth network and has connected to a cellular network;

compressing the high fidelity motion data in response to detecting the disconnecting from the high bandwidth network and while a trigger condition is not met, the trigger condition comprising one of a geo-fence breach or a timer expiry, wherein compressing the high fidelity motion data comprises:

identifying a subset of the high fidelity motion data, selecting one or more of the plurality of axes,
calculating a rate of change for the selected axis, and
calculating a summary of activity based on the calculated rate of change for the selected axis, the summary of activity representing a categorization of the activity;
transmitting the compressed high fidelity motion data to a server using the cellular network if the network adapter is not connected to the high bandwidth network and while the trigger condition is not met; and
transmitting the high fidelity motion data to the server over the cellular network upon detecting that the trigger condition was met, the trigger condition detected while compressing the high fidelity motion data.

2. The method according to claim 1 wherein receiving high fidelity motion data from a motion sensing device comprises receiving high fidelity motion data from one or more accelerometers.

3. The method according to claim 2 wherein the high fidelity motion data comprises acceleration data collected for at least one axis.

4. The method according to claim 1 wherein receiving high fidelity motion data from a motion sensing device comprises receiving high fidelity motion data according to a predefined interval.

5. The method according to claim 1 wherein a high bandwidth network comprises at least one of a wireless-fidelity (Wi-Fi) or Bluetooth network.

6. The method according to claim 1 wherein the trigger condition further comprises one of a system reset or manual push.

7. The method according to claim 1 further comprising generating a plurality of activity visualizations based on the compressed high fidelity motion data.

8. The method according to claim 7 further comprising updating the plurality of activity visualizations after transmitting high fidelity motion data corresponding to the compressed high fidelity motion data.

9. An apparatus for compressing and transmitting motion data, the apparatus comprising:
a processor; and
a non-transitory memory storing computer-executable instructions therein that, when executed by the processor, cause the apparatus to:
receive high fidelity motion data from a motion sensing device, the high fidelity motion data including a plurality of motion data samples for a plurality of axes;
store the high fidelity motion data received from the motion sensing device;
determine whether a network adapter is connected to a high bandwidth network;
transmit the high fidelity motion data to a server if the network adapter is connected to the high bandwidth network;
detect that the network adapter has disconnected from the high bandwidth network and has connected to a cellular network;
compress the high fidelity motion data in response to detecting the disconnecting from the high bandwidth network and while a trigger condition is not met, the trigger condition comprising one of a geo-fence breach or a timer expiry, wherein compressing the high fidelity motion data comprises:
identifying a subset of the high fidelity motion data,
selecting one or more of the plurality of axes,
calculating a rate of change for the selected axis, and
calculating a summary of activity based on the calculated rate of change for the selected axis, the summary of activity representing a categorization of the activity;
transmit the compressed high fidelity motion data to a server using the cellular network if the network adapter is not connected to the high bandwidth network and while the trigger condition is not met; and
transmit the high fidelity motion data to the server over the cellular network upon detecting that the trigger condition was met, the trigger condition detected while compressing the high fidelity motion data.

10. The apparatus according to claim 9 wherein receiving high fidelity motion data from a motion sensing device comprises receiving high fidelity motion data from one or more accelerometers.

11. The apparatus according to claim 10 wherein the high fidelity motion data comprises acceleration data collected for at least one axis.

12. The apparatus according to claim 9 wherein receiving high fidelity motion data from a motion sensing device comprises receiving high fidelity motion data according to a predefined interval.

13. The apparatus according to claim 9 wherein a high bandwidth network comprises at least one of a wireless-fidelity (Wi-Fi) or Bluetooth network.

14. The apparatus according to claim 9 wherein the trigger condition further comprises one of a system reset or a manual push.

15. The apparatus according to claim 9 wherein the non-transitory memory further stores computer-executable instructions therein that, when executed by the processor, cause the apparatus to generate a plurality of activity visualizations based on the compressed high fidelity motion data.

16. The apparatus according to claim 15 wherein the non-transitory memory further stores computer-executable instructions therein that, when executed by the processor, cause the apparatus to update the plurality of activity visualizations after transmitting high fidelity motion data corresponding to the compressed high fidelity motion data.

17. A system for compressing and transmitting motion data, the system comprising:
a tracking device, connected to a network, configured to:
receive high fidelity motion data from a motion sensing device, the high fidelity motion data including a plurality of motion data samples for a plurality of axes;
store the high fidelity motion data received from the motion sensing device;
determine whether a network adapter is connected to a high bandwidth network;
transmit the high fidelity motion data to a server if the network adapter is connected to the high bandwidth network;
detect that the network adapter has disconnected from the high bandwidth network and has connected to a cellular network;
compress the high fidelity motion data in response to detecting the disconnecting from the high bandwidth network and while a trigger condition is not met, the trigger condition comprising one of a geo-fence breach or a timer expiry, wherein compressing the high fidelity motion data comprises:
identifying a subset of the high fidelity motion data,
selecting one or more of the plurality of axes, calculating a rate of change for the selected axis, and
calculating a summary of activity based on the calculated rate of change for the selected axis, the summary of activity representing a categorization of the activity;
transmit the compressed high fidelity motion data to a server using the cellular network if the network adapter is not connected to the high bandwidth network and while the trigger condition is not met; and
transmit the high fidelity motion data to the server over the cellular network upon detecting that the trigger condition was met, the trigger condition detected while compressing the high fidelity motion data;
a server, connected to the network, configured to:
receive high fidelity and low fidelity motion data from a tracking device;
generate one or more visualizations based on the received high fidelity and low fidelity motion data; and
transmit the one or more visualizations to a mobile device.

* * * * *